(12) United States Patent
Yamashita et al.

(10) Patent No.: US 10,954,531 B2
(45) Date of Patent: Mar. 23, 2021

(54) METHODS AND COMPOSITIONS FOR REFINING MOLYBDENUM MINERAL

(71) Applicants: SHIBAURA INSTITUTE OF TECHNOLOGY, Tokyo (JP); JX NIPPON MINING & METALS CORPORATION, Tokyo (JP)

(72) Inventors: Mitsuo Yamashita, Tokyo (JP); Akira Miura, Hitachi (JP)

(73) Assignees: SHIBAURA INSTITUTE OF TECHNOLOGY, Tokyo (JP); JX NIPPON MINING & METALS CORPORATION, Tokyo (JP)

( * ) Notice: Subject to any disclaimer, the term of this patent is extended or adjusted under 35 U.S.C. 154(b) by 0 days.

(21) Appl. No.: 16/307,377

(22) PCT Filed: Jun. 6, 2017

(86) PCT No.: PCT/JP2017/021026
§ 371 (c)(1),
(2) Date: Dec. 5, 2018

(87) PCT Pub. No.: WO2017/213152
PCT Pub. Date: Dec. 14, 2017

(65) Prior Publication Data
US 2019/0309325 A1    Oct. 10, 2019

(30) Foreign Application Priority Data
Jun. 6, 2016 (JP) .............................. JP2016-112987

(51) Int. Cl.
| | |
|---|---|
| *B01D 15/08* | (2006.01) |
| *C12P 3/00* | (2006.01) |
| *C12N 7/00* | (2006.01) |
| *C12N 15/86* | (2006.01) |
| *C07K 7/06* | (2006.01) |
| *C07K 7/08* | (2006.01) |
| *C12N 15/09* | (2006.01) |

(52) U.S. Cl.
CPC ............. *C12N 15/86* (2013.01); *B01D 15/08* (2013.01); *C07K 7/06* (2013.01); *C07K 7/08* (2013.01); *C12N 15/09* (2013.01); *C12P 3/00* (2013.01); *B01D 2257/60* (2013.01); *C12N 7/00* (2013.01); *C12N 2750/00041* (2013.01)

(58) Field of Classification Search
None
See application file for complete search history.

(56) References Cited

U.S. PATENT DOCUMENTS

| 2012/0122669 A1 | 5/2012 | Matsukawa |
| 2019/0345200 A1 | 11/2019 | Yamashita et al. |

FOREIGN PATENT DOCUMENTS

| JP | 10-338700 A | 12/1998 |
| JP | 3277532 B2 | 4/2002 |
| JP | 2014-188428 A | 10/2014 |
| JP | 2015-224225 A | 12/2015 |
| JP | 2016-47810 A | 4/2016 |
| WO | WO 2010/134140 A1 | 11/2010 |

OTHER PUBLICATIONS

Warner et al., Bioprocess Biosyst Eng, 2014, 37:2067-2072. (Year: 2014).*
Dickerson et al., "Identification of peptides that promote the rapid precipitation of germania nanoparticle networks via use of a peptide display library", Chem. Commun., 2004, No. 15, pp. 1776-1777.
Imai, "Development in Column Flotation Technologies", Resources Processing, 2000, vol. 47, No. 1, pp. 14-21.
International Search Report, issued in PCTIJP2017/021026, dated Aug. 29, 2017.
International Preliminary Report on Patentability and Written Opinion of the International Searching Authority(Forms PCT/IB/338, PCT/IB/373 and PCT/ISA/237), dated Dec. 20, 2018, for International Application No. PCT/JP2017/021026.
English translation of Imai, "Development in Column Flotation Technologies", Resources Processing, 2000, vol. 47, No. 1, pp. 14-21 (22 pages total).

* cited by examiner

*Primary Examiner* — Nicole Kinsey White
(74) *Attorney, Agent, or Firm* — Birch, Stewart, Kolasch & Birch, LLP

(57) ABSTRACT

Improved methods and compositions for refining molybdenum mineral are provided, in particular for isolating a substance containing molybdenum which comprises contacting the substance containing molybdenum with a composition comprising a M13 phage. The M13 phage provides selectivity and recovery of the substance containing molybdenum.

6 Claims, 5 Drawing Sheets
(4 of 5 Drawing Sheet(s) Filed in Color)
Specification includes a Sequence Listing.

[Fig 1]
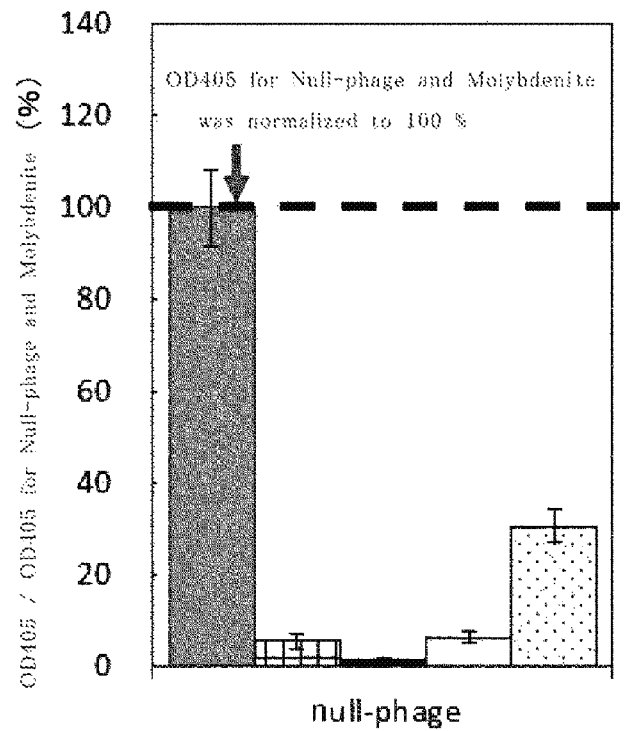
[Fig 2]
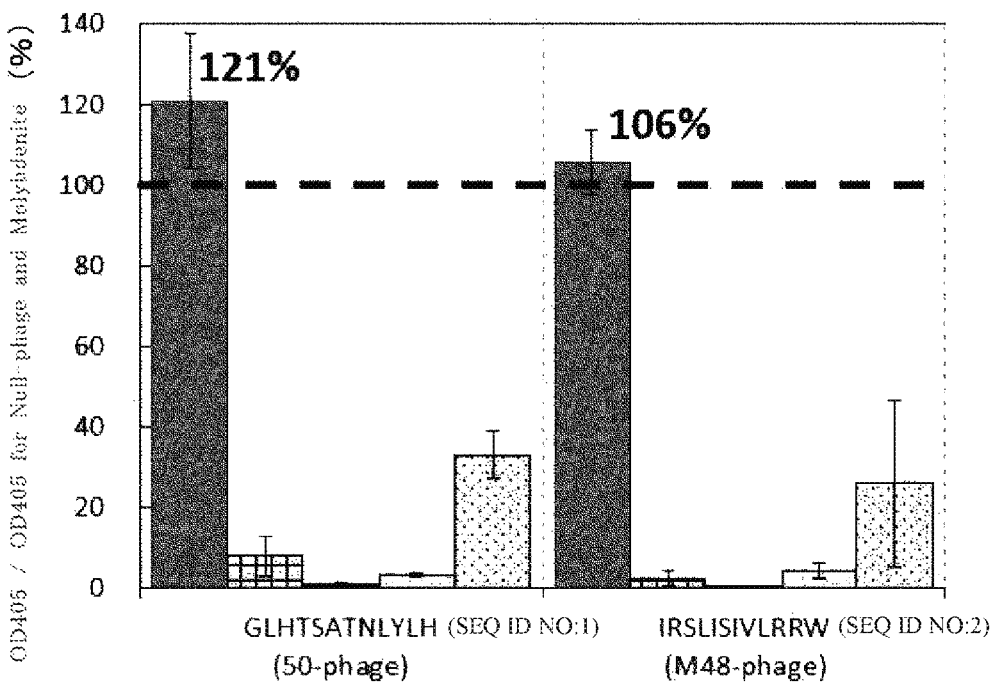

[Fig 3]
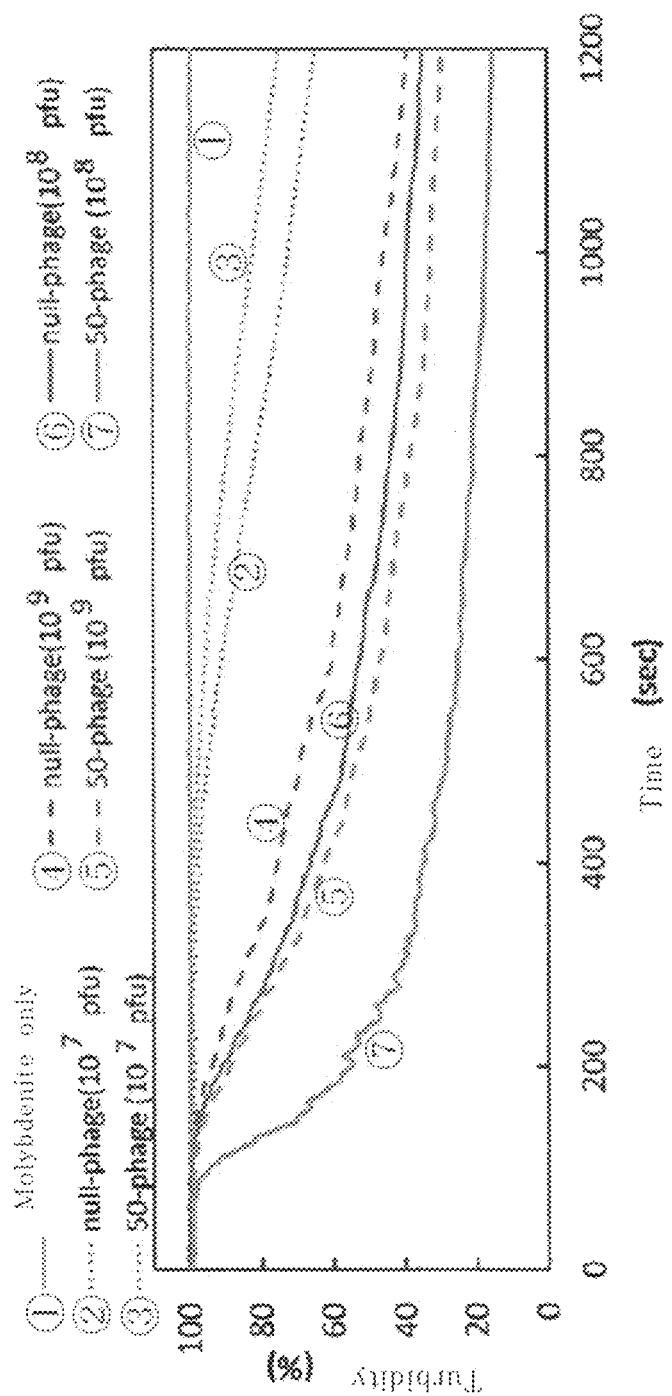

[Fig 4]
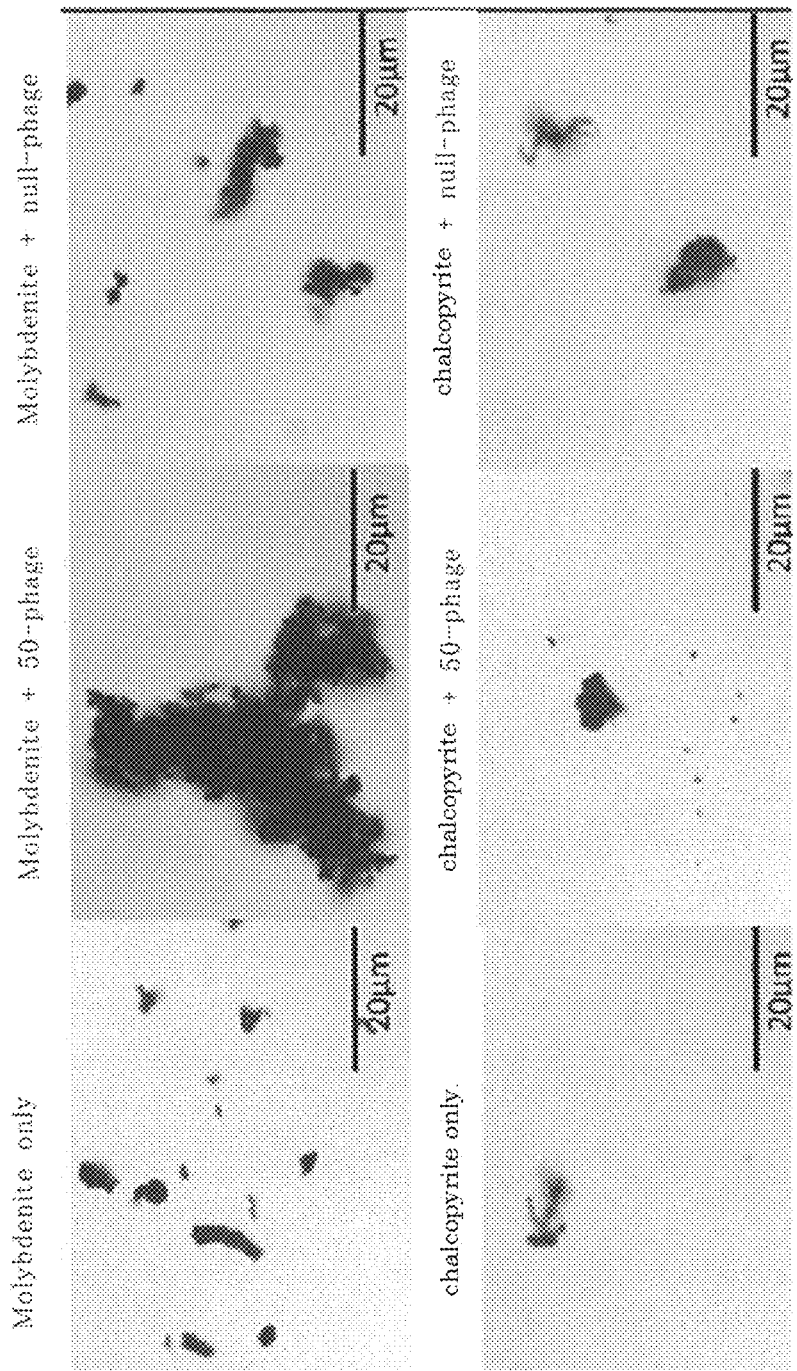

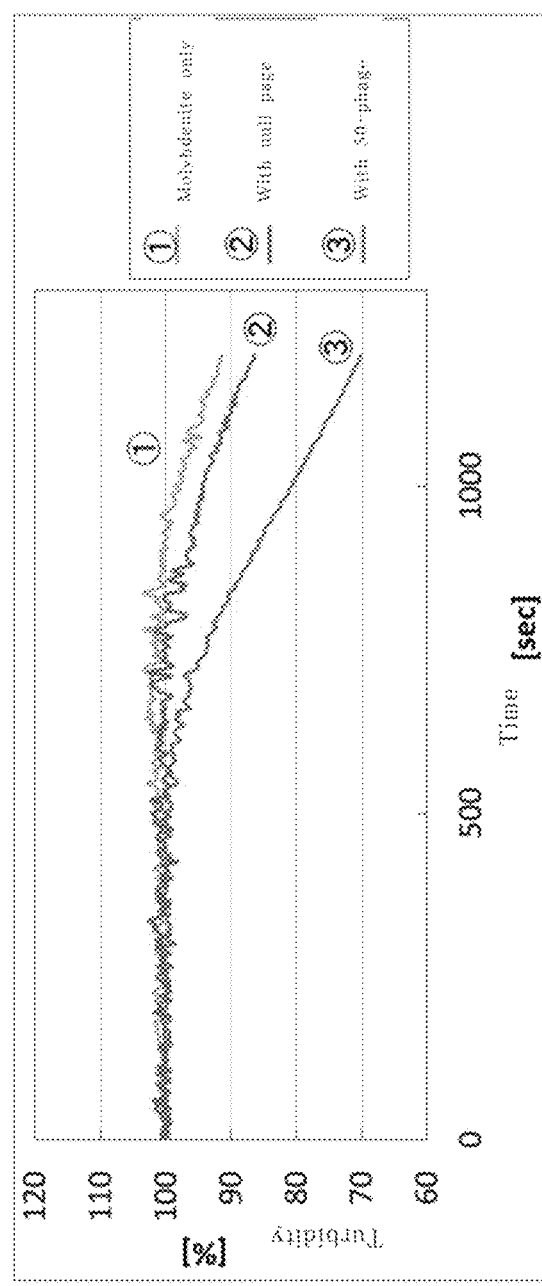
[Fig 5]

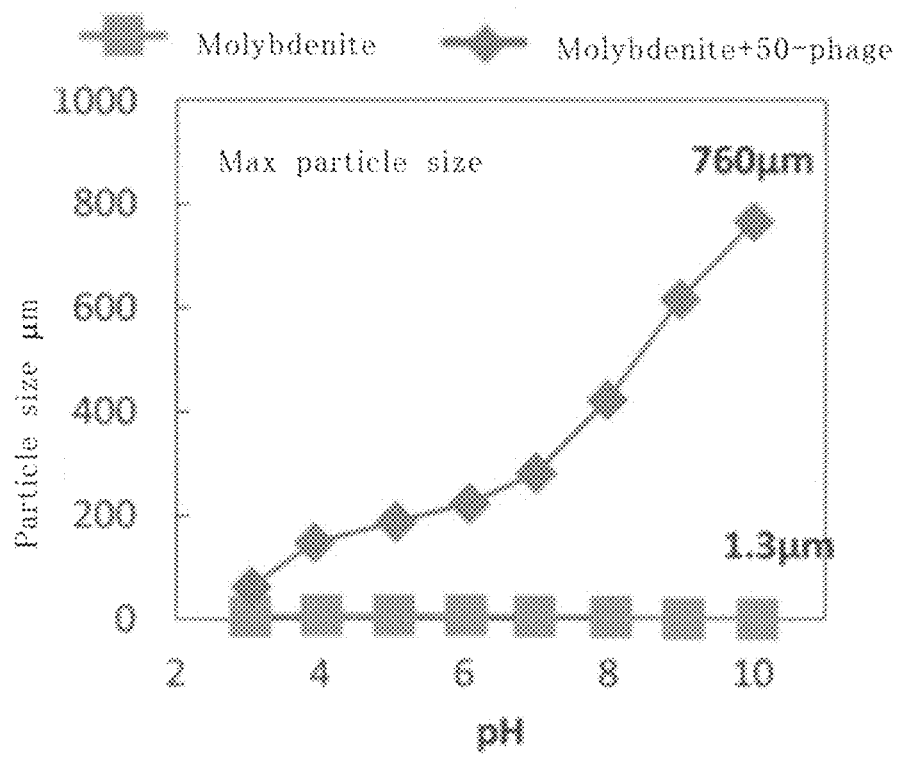
[Fig 6]

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Ramdomly synthesized peptide

<400> SEQUENCE: 1

Gly Leu His Thr Ser Ala Thr Asn Leu Tyr Leu His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Randomly synthesized peptide

<400> SEQUENCE: 2

Ile Arg Ser Leu Ile Ser Ile Val Leu Arg Arg Trp
1               5                   10

US 10,954,531 B2

METHODS AND COMPOSITIONS FOR REFINING MOLYBDENUM MINERAL

FIELD OF INVENTION

The present invention is related to virus composition and a method for separation using the same. In particular, the present invention is related to composition comprising virus specifically biding to a certain chemical element and a method for separation using the same.

TECHNICAL BACKGROUND

Molybdenum is a valuable chemical element, which is used for such as an ingredient of an alloy of special steel, catalyst for purifying oil, and lubricant. Molybdenum often exists in Porphyry copper deposit etc., in which copper sulfide ores exist in accompany with molybdenite as an sulfide mineral, which is recovered as molybdenum concentrate. The molybdenum concentrate mined from Porphyry copper deposit is recovered as byproduct of froth floatation in the process of concentrating and/or refining copper sulfide mineral. The molybdenite tends to float, and thus it can easily float by adding a frother in addition to a collector such as kerosene and diesel oil. However, since an copper sulfide mineral, which is accompanied with molybdenite, also tends to float, it is required to add cyanide and/or sodium hydrogen sulfide for the purpose of suppressing float of copper sulfide minerals.

However, the drawbacks of these are: that cyanide has a risk of environmental pollution by its toxicity; and that the presence of sodium hydrogen sulfide leads to production of hydrogen sulfide when mineral slurry is acidic.

Patent document 1 discloses a method for refining molybdenum mineral without use or occurrence of toxic substances, in which oxidation of ozone is applied. Patent document 2 discloses a method for utilizing plasma irradiation. Patent document 3 discloses an amino acid is supported by a carrier to recover a molybdenum compound.

[List of Patent Literature]

[Patent Literature 1] Japanese patent number 3277532

[Patent Literature 2] Unexamined Japanese patent publication number 2014-188428

[Patent Literature 3] Unexamined Japanese patent publication number 2015-224225

SUMMARY OF INVENTION

Technical Problem

In the above disclosed methods, specialized devices are required for utilizing ozone or irradiating plasma, both of which are impractical, and thus neither of them has not been realized yet.

An object of the present invention is to provide novel methods for isolating a substance containing molybdenum.

Solution to Problem

In light of the above object, the present inventors have studied intensively and found that certain phage can selectively bind to molybdenite.

On the basis of the above discovery, in one aspect, the present invention includes the following inventions.

(Invention 1)
Composition comprising M13 phage for separating a substance containing molybdenum.

(Invention 2)
A method of separating a substance containing molybdenum, using the composition of Invention 1.

(Invention 3)
A method of Invention 2, wherein the substance containing molybdenum is molybdenite.

(Invention 4)
A method of Invention 2 or 3, comprising: adding the composition to liquid in which substances containing molybdenum disperse;
aggregating and precipitating the substances containing molybdenum; and
recovering the aggregated and precipitated substances.

(Invention 5)
A method of Invention 2 or 3, comprising:
affixing to a carrier, M13 phage in the composition;
introducing the carrier into a column for chromatography; and passing through the column, liquid in which substances containing molybdenum disperse.

(Invention 6)
A method of Invention 2 or 3, comprising:
affixing to a particle, M13 phage in the composition; and introducing the particle into liquid in which substances containing molybdenum disperse.

(Invention 7)
A method of Invention 2 or 3, the method comprising froth floating with use of M13 phage in the composition.

(Invention 8)
Composition comprising M13 phage vector, wherein the composition is for preparing the composition of Invention 1.

(Invention 9)
M13 phage comprising a peptide comprising a sequence according to any one of the following sequences (1) and (2):

```
(1)
(A, L, R, K, N, M, D, F, C, P, Q, S, E, T, G,

W, H, Y, I, or V)-(L, I, V, F, or A)-(H, P,

W, R, or K)-(T, S, N, or Q)-(T, S, N, or Q)-

(L, I, V, F, or A)-(T, S, N, or Q)-(T, S, N, or Q)-(L, I, V, F, or A)-(F, Y, or W)-(L, I,

V, F, or A)-(H, P, W, R, or K)

(2)
(L, I, V, F, or A)-(R, H, or K)-(T, S, N, or

Q)-(L, I, V, F, or A)-(L, I, V, F, or A)-(T,

S, N, or Q)-(L, I, V, F, or A)-(L, I, V, F, or A)-(L, I, V, F,  or A)-(R, H, or K)-(R, H, or K)-(H, P, or W)
``` wherein one amino acid is respectively selected from each group defined by paired parentheses.

(Invention 10)
Phage of Invention 9, comprising a peptide comprising a sequence according to any one of the following sequences (A) and (B):

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 11)

Phage of Invention 9, comprising a peptide according to any one of the following sequences (A) and (B):

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 12)

Phage of Invention 9, comprising a peptide comprising a sequence which is at least 90% identical to any one of the following sequences (A) and (B):

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 13)

Phage of Invention 9, comprising a peptide comprising a sequence which is at least 95% identical to any one of the following sequences (A) and (B):

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 14)

Phage of Invention 9, comprising a peptide comprising a sequence which is at least 98% identical to any one of the following sequences (A) and (B):

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 15)

Phage of Invention 9, comprising a peptide comprising a sequence derived from at least any one of the following sequences (A) and (B) by deleting, replacing, and/or adding 1-5 amino acid:

```
                                                    (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

(Invention 16)

M13 phage comprising a nucleic acid encoding the amino acid sequence according to any one of Inventions 9-15.

(Invention 17)

M13 phage comprising a nucleic acid comprising a sequence which is at least 90% identical to a nucleic acid sequence encoding the peptide of any one of Inventions 9-15.

(Invention 18)

M13 phage vector, comprising a nucleic acid encoding the amino acid sequence according to any one of Inventions 9-15.

Effect of Invention

In one aspect, the present invention utilizes phage. Thereby, it does not require a large scale of devices comparing to conventional techniques. Also, it does not require using toxic compounds or any compounds that have a risk of producing toxic compounds, such as cyanide and sodium hydrogen sulfide. Furthermore, the phage utilized in the present invention corresponds to P1 level. Thus, safe isolation is possible.

Furthermore, the phage according to the present invention enable to isolate efficiently. Moreover, a mineral of interest can be selectively isolated.

BRIEF DESCRIPTION OF DRAWINGS

The patent or application file contains at least one color drawing. Copies of this patent or patent application publication with color drawing will be provided by the USPTO upon request and payment of the necessary fee.

FIG. 1 is a graph showing that the phage according to one embodiment of the present invention can selectively bind to a certain mineral. Five bars in each group represent, in the order from left to right, OD405 of molybdenite, elemental sulfur, chalcopyrite, enargite, and pyrite respectively.

FIG. 2 is a graph showing that the peptides according to one embodiment of the present invention can selectively bind to a certain mineral. Five bars in each group represent, in the order from left to right, OD405 of molybdenite, elemental sulfur, chalcopyrite, enargite, and pyrite respectively.

FIG. 3 is a graph showing that turbidity changes when molybdenite is precipitated with use of 50-phage etc. according to one embodiment of the present invention.

FIG. 4 is a photograph showing a size of particles when molybdenite is precipitated with use of 50-phage etc. according to one embodiment of the present invention.

FIG. 5 is a graph showing that turbidity changes when molybdenite is precipitated with use of 50-phage etc. according to one embodiment of the present invention.

FIG. 6 is a graph showing that a maximum size of particle changes when molybdenite is precipitated with use of 50-phage etc. according to one embodiment of the present invention. This change depends on pH.

DESCRIPTION OF EMBODIMENTS

Now, for the purpose of enhancing the understanding of the present invention, more specified embodiments are described hereinafter, which are not intended to limit the scope of the present invention.

1. Applicable Substances

In one embodiment, the present invention can be applicable to a method for isolating a certain substance. The certain substance may include a substance containing molybdenum. More specifically, in one embodiment, the present invention can be applicable to a method for isolating a mineral containing molybdenum. A mineral containing molybdenum may include molybdenite, wulfenite, powellite, ferrimolybdite etc. A typical example for a mineral containing molybdenum includes molybdenite since it is commonly mined.

2. Virus

In one embodiment of the present invention, certain virus is provided. Specifically, M13 phage is provided. M13 phage may be provided such that it is contained in composition (e.g., containing buffer (Tris etc.) and/or EDTA). M13 phage or composition containing M13 phage may be utilized for the purpose of separating a substance containing molybdenum.

M13 phage per se is typically used in genetic engineering technique such as phage display. The inventors have discovered a feature of M13 phage that has been ever unknown in the prior art. Specifically, the inventors have discovered that M13 phage can bind to a substance containing molybdenum (e.g., molybdenite). Furthermore, the inventors have discovered that M13 phage can selectively bind to molybdenite without binding to other minerals.

M13 phage used in the present invention may incorporate other genes with genetic engineering technique. Alternatively, it may be the one without incorporating any other genes.

3. How to Use

Utilizing such an unknown feature, the following applications may be possible in one embodiment.

3-1. Precipitation of a Substance of Interest

In one embodiment, the present invention includes M13 phage, or composition containing M13 phage. The composition may be added into suspension in which substances of interest disperse. After adding, M13 phage can bind the substances of interest, aggregate them, and ultimately precipitate them. Then, the precipitation may be recovered.

3-2. Binding to a Particle

In one embodiment, the present invention includes a particle binding to M13 phage. An example for a particle may include beads (e.g., magnetic beads, glass beads, high-molecular beads etc.), and a carrier and etc. A size of a particle is not limited, and may be adjusted depending on its usage. M13 phage may be bound to a surface of a particle by technique known in the art.

In the present invention, a substance of interest may be isolated with use of a particle binding to M13 phage. For example, a substance of interest may be bound to M13 phage and precipitated to be isolated.

3-3. Column for Purification

A substance of interest may be isolated via column chromatography. Column chromatography relies on property where a column (or functional groups on inner surface of column) selectively binds to a certain substance. In one embodiment of the present invention, the above described M13 phage can be affixed to a carrier and then the carrier may be introduced into a column. Utilizing such a column, a substance of interest may be isolated.

3-4. Collector for Froth Flotation

Froth flotation is a method for separation by trapping particles via bubble. In this method, a collector may be used. In one embodiment of the present invention, if M13 phage is easily trapped by bubble, M13 phage itself may be used as a collector. Alternatively, M13 phage may be bound to a collector or a frother known in the art, to enhance the trap by bubble. Thereby, a substance of interest may be trapped by bubble and consequently be isolated.

3-5. An Amount of Phage

Regarding to the above described usage or other usage, an amount of M13 phage is not particularly limited to a certain amount. The amount may be appropriately set for each of usage. For example, if using M13 phage per se or composition containing M13 phage to recover particles of minerals, an amount of phage is $0.5 \times 10^8$ pfu/mL-$5 \times 10^8$ pfu/mL, more preferably $0.6 \times 10^8$ pfu/mL-$1.5 \times 10^8$ pfu/mL in relative to 3 g/L of mineral particles. Alternatively, an amount of phage may be $0.5 \times 10^9$ pfu/mL-$5 \times 10^9$ pfu/mL, more preferably $0.6 \times 10^9$ pfu/mL-$1.5 \times 10^9$ pfu/mL in relative to 10 g/L of mineral particles. Alternatively, the ratio of an amount of phage (pfu/mL)/an amount of minerals (g/L) is $0.13 \times 10^8$-$5 \times 10^8$, more preferably $0.33 \times 10^8$-$1 \times 10^8$.

4. Application (Methods of Separation)

Now methods for the above application are described hereinafter.

4-1. Substances to be Isolated

The above described embodiments for application are related to isolating a certain substance. In these embodiments, a substance to be isolated may be molybdenum. For example, the above described molybdenum-containing mineral (e.g., molybdenite) may be isolated.

4-2. A Method of Isolation Using M13 Phage or Composition Containing M13 Phage

In one embodiment of the present invention, M13 phage or composition containing M13 phage may be used to separate substances (specifically, a molybdenum-containing mineral, more specifically, molybdenite). For example, suspension in which substances to be separated disperse is prepared. Then, M13 phage or composition containing M13 phage may be added. After adding, M13 phage may bind to the substances to be separated, aggregate them, and ultimately precipitate them. Then, the precipitation may be recovered.

4-3. A Method for Isolating by Column Chromatography

In one embodiment of the present invention, via column chromatography, a substance (specifically, molybdenum-containing mineral, more specifically, molybdenite) may be isolated. In this procedure, initially, M13 phage may be affixed to a carrier by technique known in the art. Then, the carrier may be introduced into column for purification. After preparing the column, liquid in which a substance disperses is passed through the column. Then the substance binds to inside of the column, and/or elution of the substance is delayed. Thereby, the substance of interest may be isolated.

4-4. A Method for Isolating by a Particle

In one embodiment of the present invention, using a particle, a substance (specifically, molybdenum-containing mineral, more specifically, molybdenite) may be isolated. Initially, M13 phage may be affixed to the surface of the particle by technique known in the art. Then, the particle may be introduced into mineral dispersion (liquid in which mineral particles are dispersed). Introducing the particle and then leaving it for a while, phage on the surface of the particle bind to mineral particles to be aggregated and then to be precipitated. After this, the precipitated mineral on the bottom may be recovered. Alternatively, a particle may be a magnetic bead, and without waiting for precipitation, mineral particle may be recovered by magnetic power.

4-5. A Method for Froth Flotation

In one embodiment of the present invention, using a collector and/or a frother, a substance (specifically, molybdenum-containing mineral, more specifically, molybdenite) may be isolated. Specifically, a collector and/or a frother are bound to M13 phage by technique known in the art. Then, the bound collector and/or frother is introduced into solution to be agitate (other agent may be introduced appropriately), and to form bubble. After this, mineral particles are introduced to be trapped by the bubble. Thereby, mineral particles may be recovered. Alternatively, M13 phage per se may be used as a collector.

5. Selectivity for Biding to Mineral

As described above, M13 phage has a feature of selectivity that they are capable of strongly binding to a certain ores, but do not bind to other minerals. More specifically, they are capable of strongly binding to a molybdenum-containing mineral (e.g., molybdenite), but do not bind to other minerals such as elemental sulfur, chalcopyrite, enargite, pyrite (alternatively, are capable of biding to other minerals with significantly less strength comparing to those of a molybdenum-containing mineral). Thus, even if it is a mixture of a molybdenum-containing mineral and other minerals, a molybdenum-containing mineral may be isolated by the above methods.

6. M13 Phage Virus Vector

In one embodiment, the present invention provides a certain virus vector. More specifically, the present invention provides a M13 phage virus vector. This vector may be provided such that it is contained in composition (e.g., containing buffer (Tris etc.) and/or EDTA). Then, M13 phage vector or composition containing a M13 phage vector may be utilized for preparing M13 phage or composition containing M13 phage. Then, the prepared M13 phage or composition containing M13 phage may be utilized for the purpose of separating a substance containing molybdenum.

M13 phage vector per se may be purified from M13 phage, or may be available from merchants (such as, M13mp18-Single Stranded Phage DNA (Product code P-107) available from BAYOU BioPlus inc. or M13 mp18 RF DNA (product code 3118) available from TakaraBio).

7. Peptide

For the purpose of isolating the substance described above, in one embodiment of the present invention, a peptide can be used in combination with M 13 phage (or M13 phage vector), thereby enhancing the function of isolating a substance containing molybdenum. In particular, it enables to enhance the function of selectively isolating mineral containing molybdenum. More specifically, a peptide can be used that includes an amino acid sequence according the following formula (1) and/or (2). Typically, certain number of amino acid can be added in their N terminal and/or C terminal. The certain number may fall within numerical range defined by two numbers selected from 1, 2, 3, 4, 5, 6, 7, 8, 9, 10, 15, and 20 (e.g., from 1 to 10, or from 5 to 20).

(1)
(A, L, R, K, N, M, D, F, C, P, Q, S, E, T, G, W, H, Y, I, or V)-(L, I, V, F, or A)-(H, P, W, R, or K)-(T, S, N, or Q)-(T, S, N, or Q)-(L, I, V, F, or A)-(T, S, N, or Q)-(T, S, N, or Q)-(L, I, V, F, or A)-(F, Y, or W)-(L, I, V, F, or A)-(H, P, W, R, or K)

(2)
(L, I, V, F, or A)-(R, H, or K)-(T, S, N, or Q)-(L, I, V, F, or A)-(L, I, V, F, or A)-(T, S, N, or Q)-(L, I, V, F, or A)-(L, I, V, F, or A)-(L, I, V, F, or A)-(R, H, or K)-(R, H, or K)-(H, P, or W)

(wherein one amino acid is respectively selected from each group defined by paired parentheses)

The working examples described hereinafter show the peptides according to the following amino acid sequences were used to isolate molybdenite.

(SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp

The above amino acid sequences of (1) and (2) and the above amino acid sequences of (A) and (B) correspond as follows.

TABLE 1

|    | (A) | (1) |
|----|-----|-----|
| 1  | Gly | (A, L, R, K, N, M, D, F, C, P, Q, S, E, T, G, W, H, Y, I, or V) |
| 2  | Leu | (L, I, V, F, or A) |
| 3  | His | (H, P, W, R, or K) |
| 4  | Thr | (T, S, N, or Q) |
| 5  | Ser | (T, S, N, or Q) |
| 6  | Ala | (L, I, V, F, or A) |
| 7  | Thr | (T, S, N, or Q) |
| 8  | Asn | (T, S, N, or Q) |
| 9  | Leu | (L, I, V, F, or A) |
| 10 | Tyr | (F, Y, or W) |
| 11 | Leu | (L, I, V, F, or A) |
| 12 | His | (H, P, W, R, or K) |

TABLE 2

|    | (B) | (2) |
|----|-----|-----|
| 1  | Ile | (L, I, V, F, or A) |
| 2  | Arg | (R, H, or K) |
| 3  | Ser | (T, S, N, or Q) |
| 4  | Leu | (L, I, V, F, or A) |
| 5  | Ile | (L, I, V, F, or A) |
| 6  | Ser | (T, S, N, or Q) |
| 7  | Ile | (L, I, V, F, or A) |
| 8  | Val | (L, I, V, F, or A) |
| 9  | Leu | (L, I, V, F, or A) |
| 10 | Arg | (R, H, or K) |
| 11 | Arg | (R, H, or K) |
| 12 | Trp | (H, P, or W) |

As shown in Table 1, the first amino acid in the sequence (A) is glycine. Since the residue of glycine is (—H), it is not likely that the residue itself contributes to certain function.

Thus, even if replacing glycine with the other natural amino acids, the peptide will retain same or similar property.

The second amino acid in the sequence (A) is leucine, which is a hydrophobic amino acid. Thus, even if replacing with isoleucine, valine, phenylalanine, alanine, etc., which are also hydrophobic, the peptide will retain same or similar property.

The third amino acid in the sequence (A) is histidine. Histidine has heterocyclic ring in its residue. Thus, even if replacing with tryptophan or proline, which also have heterocyclic ring in their residue, the peptide will retain same or similar property. Furthermore, histidine is polar-charged (basic) amino acid. Thus, even if replacing with arginine or lysine, which are also polar-charged(basic) amino acids, the peptide will retain same or similar property.

The 4th and 5th amino acids in the sequence (A) are threonine and serine respectively. These are a polar non-charged amino acid. Thus, even if replacing with threonine, serine, asparagine, or glutamine, which are also polar non-charged amino acids, the peptide will retain same or similar property.

The 10th amino acid in the sequence (A) is tyrosine, which is an aromatic amino acid. Thus, even if replacing with tryptophan or phenylalanine, which are also aromatic amino acids, the peptide will retain same or similar property.

The second amino acid in the sequence (B) is arginine, which has a basic residue. Thus, even if replacing with lysine or histidine, which are also basic amino acids, the peptide will retain same or similar property.

As similar to the above, the other amino acids can be replaced on the basis of the same or similar point of view (e.g., hydrophobic-hydrophilic, acidic-neutral-basic, common functional group, etc.).

In one embodiment, the present invention encompasses the peptides including at least any one of the following sequences.

```
                                          (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

Additionally, an arbitrary number of amino acid can be added in their N terminal and/or C terminal. Typically, the arbitrary number may fall within numerical range defined by two numbers selected from 1, 2, 3, 4, 5, 6, 7, 8, 9, 10, 15, and 20 (e.g., from 1 to 10, or from 5 to 20).

In one embodiment, the present invention encompasses the peptides represented by any one of the following 12-amino acid sequences.

```
                                          (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

Regarding to the above amino acid sequences (A) and (B), even if making a slight modification (e.g., insertion, replacement, and/or addition of amino acid), the modified peptide will retain property that is the same as or similar to those of amino acids sequences (A) and/or (B). For example, a peptide or a peptide including a sequence which is 66% or more, 75% or more, 83% or more, 90% or more, 95% or more, 98% or more, or 99% or more identical to the amino acids sequences (A) and/or (B), will also retain the same or similar property.

A numerical value for sequence similarity can be calculated by technique known in the art. For example, the value may be calculated based on a value derived by Blastp, which is used for homology search of amino acids (or protein) and is provided by BLAST (Trademark)

In one embodiment, the present invention encompasses a peptide comprising a sequence derived from at least any one of the following sequences (A) and (B) by deleting, replacing, and/or adding 1-5 amino acid, typically, by deleting, replacing, and/or adding 4 or less, 3 or less, or 2 or less amino acids.

```
                                          (SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp
```

8. Nucleic Acid Encoding Peptide

In one embodiment, the present invention encompasses a nucleic acid encoding at least any one of the above peptides. The nucleic acid may be DNA or RNA. In one embodiment, the present invention encompasses a nucleic acid having a sequence being complimentary to a sense strand encoding at least any one of the above peptides.

In one embodiment, the present invention encompasses a nucleic acid comprising a sequence which is at least 80% or more, 85% or more, 90% or more, 95% or more, or 98% or more identical to a nucleic acid sequence encoding to at least any one of the above peptides. As similar to the case of amino acids sequence, a numerical value for sequence similarity can be calculated by technique known in the art. For example, the value may be calculated based on a value derived from a search result by Blastn, which is provided by BLAST Moreover, in one embodiment, the present invention encompasses a nucleic acid being capable of hybridizing with a sequence being complimentary to sense strand of a nucleic acid encoding at least any one of the above peptides. More specifically, the present invention encompasses the nucleic acid being capable of hybridizing under a stringent condition. The stringent condition may be a condition known in the art. For example, it may be a condition that is disclosed in Japanese patent publication No. 2015-023831. More specifically, it may be judged through the following procedure: using a filter in which DNA is fixed; hybridization in the presence of 0.7-1.0 M of NaCl under the temperature 65 degree Celsius; and washing a filter at the temperature of 65 degree Celsius, by 0.1-2×SSC (saline-sodium citrate) solution (1×SSC solution contains 150 mM NaCl, 15 mM Sodium citrate).

Any of the above described nucleic acids are usable for preparing a peptide of interest through genetic engineering technique. For example, any one or more of the above described nucleic acids may be introduced into expression vector to express a peptide of interest in a large scale. Alternatively, a phage having a peptide of interest on its surface may be prepared through a phage display method described hereinafter.

If the nucleic acids are DNA (and if the nucleic acids are coding strand), the nucleic acids may be introduced into a virus vector of M13 phage.

9. pH Dependency

In the procedure of binding the above described peptides to a molybdenum-containing mineral (e.g., molybdenite), adjusting pH of liquid to certain range can enhance binding (and aggregation). Specifically, as pH increases, maximum size of particles in particle distribution of liquid can increase. For example, within the pH range from 4 to 12, preferably within the pH range 5 or more, maximum size of particles can increase.

EXAMPLES

Now, via the following working examples, the above described embodiments of the present invention are described more specifically, although the scope of the present invention is not limited to the following working examples.

(Example 1) ELISA Analysis for Molybdenite-Binding Phage

M13 phage is usually used for a phage display method. Further, M13 phage may, via genetic engineering technique, display certain peptide on its surface. In the present example, M13 phage without being subjected to such genetic engineering operation (null-phage) was used.

Regarding to molybdenite and M13 phage without displaying the peptide (null-phage), ELISA analysis (Enzyme-Linked ImmunoSorbent Assay) was performed to measure an amount of binding to molybdenite. Specifically, 3000 mg/L of molybdenite were suspended and then aliquoted to each well of 96-well microplate. Each phage was added into each well, and unbound phages were washed out. After that, anti M13-phage antibody conjugated with an enzyme (peroxidase) was added and then unbound anti-phage antibodies were washed out. Next, 2,2'-azino-bis (3-ethylbenzothiazoline-6-sulphonic acid) diammonium salt (ABTS), which is the substrate for the enzyme, was added. Blue-colored samples resulting from digestion of ABTS were analyzed by a microplate reader with the wave length of 405 nm. Furthermore, the same procedure was performed with the replacement with the other minerals (elemental sulfur, chalcopyrite, enargite, and pyrite).

FIG. 1 shows a ratio of absorbance. Specifically, the absorbance of ELISA analysis under the conditions that M13-phage not having the peptides (null-phage) was contacted with molybdenite was normalized to be 100%. Then, the ratio of absorbance for each mineral was calculated (i.e., the ratio of "the amount of binding by null-phage to each mineral" in relative to "the amount of binding by null-phage to molybdenite"). As shown in FIG. 1, comparing to the amount of binding for molybdenite, M13 phage (null-phage) bound to elemental sulfur, chalcopyrite, enargite, and pyrite with a significant less amount. Thus, M13 phage (null-phage) was shown to be useful for selectively isolating molybdenite.

(Example 2) ELISA Analysis for Molybdenite-Binding Phage that Displays Peptide on its Surface ELISA analysis was performed under the similar condition to those of Example 1. However, M13 phage displaying any one of the following sequences on its surface was used.

(SEQ ID NO: 1)
(A) Gly-Leu-His-Thr-Ser-Ala-Thr-Asn-Leu-Tyr-Leu-His (SEQ ID NO: 2)
(B) Ile-Arg-Ser-Leu-Ile-Ser-Ile-Val-Leu-Arg-Arg-Trp

Hereinafter, phage displaying the peptide according to the sequence (A) on its surface is referred to as 50-phage, and phage displaying the peptide according to the sequence (B) on its surface is referred to as M48-phage. The results are shown in FIG. 2. FIG. 2 shows absorbance on the conditions that OD405 of null-phage and molybdenite in FIG. 1 was normalized to 100%. Comparing to the result shown in FIG. 1, the function of biding to molybdenite was shown to be enhanced.

(Example 3) Measurement for Precipitation Rate in the Case of Molybdenite with a Density of 3 g/L and Observation by a Microscope Under the conditions of the temperature of 30 degree Celsius, molybdenite with the particle size being 75 micrometer or less was suspended in water such that a pulp density was 3 g/L. Each of 50-phage and null-phage was added to the suspension such that each density was $10^7$-$10^9$ pfu/ml. Then, turbidity in the upper portion of the suspension was measured with a spectrophotometer (wave length 660 nm) every 5 second after adding the phages. A change of the turbidity is shown in FIG. 3 (the turbidity at the time of adding the phages (0 second), was deemed to be 100%). As a result, when 50-phage was added with the density of $10^8$ pfu/ml, the turbidity rapidly decreased, which demonstrates that the particles of molybdenite rapidly precipitated. Furthermore, the particles of molybdenite was observed by an optical microscope on the same conditions (FIG. 4), demonstrating that when 50-phage was added to molybdenite, the particles of molybdenite aggregated more significantly. These results indicate the possibility that molybdenite can be selectively isolated and recovered by adding 50-phage to suspension of molybdenite with an appropriate density.

(Example 4) Measurement of the Precipitation Rate and Observation by Microscope when Adding 50-Phage A precipitation rate after adding 50-phage was measured in the same manner as those of Example 3 except for the pulp density for molybdenite, which was 10 g/L. The result is shown in FIG. 5. On the conditions that a pulp density for molybdenite was 10 g/L and a density of 50-phage was $10^9$ pfu/ml, it was shown that molybdenite significantly precipitated.

(Example 5) a Change of Maximum Particle Size when Adding 50-Phage and its pH Dependency Under the conditions of the temperature 30 degree Celsius, molybdenite with the particle size being 75 micrometer or less was suspended in water such that a pulp density was 10 g/L. The suspension was added with 50-phage such that a density of 50-phage is $10^9$ pfu/ml. Then, pH of the suspension was adjusted to predetermined value with use of NaOH and HCl. A particle size was measured by the instruments, AcoustoSizerIIx (Kyowa Interface Science Co., Ltd.). The result was shown in FIG. 6. It was shown that as pH increased, a maximum particle size also increased. Especially in the case of pH being 4 or more, comparing to the case where only molybdenite was contained, adding 50-phage significantly increased a maximum particle size.

What is claimed is:

1. A method for isolating a substance containing molybdenum, the method comprising
   contacting a solution comprising the substance containing molybdenum with a composition comprising a M13 phage, wherein the molybdenum contained in the substance binds to the M13 phage, and
   isolating the substance containing molybdenum from the solution.

2. The method of claim 1, wherein the substance containing molybdenum is molybdenite.

3. The method of claim 1, wherein the contacting step comprises:
   adding the composition comprising the M13 phage to the solution comprising the substance containing molybdenum; and
   aggregating and precipitating the M13 phage-bound substance containing molybdenum; and wherein the step of isolating comprises:
   recovering the aggregated and precipitated substance containing molybdenum.

4. The method of claim 1, wherein the step of contacting comprises:
   passing the solution comprising the substance containing molybdenum through a chromatography column having a carrier comprising the M13 phage affixed thereto.

5. The method of claim 1, wherein the step of contacting comprises:
   introducing a particle into the solution comprising the substance containing molybdenum, wherein the particle comprises the M13 phage affixed thereto.

6. The method of claim 1, wherein the step of contacting comprises:
   froth floating the substance containing molybdenum, wherein the froth floating step comprises:
   forming bubbles in the solution; and
   trapping the substance containing molybdenum in the bubbles to allow binding between the M13 phage and the molybdenum contained in the substance.

* * * * *